United States Patent [19]
Ghosh

[11] Patent Number: 6,149,927
[45] Date of Patent: Nov. 21, 2000

[54] SOLID BIOCIDAL COMPOSITIONS

[75] Inventor: Tirthankar Ghosh, Oreland, Pa.

[73] Assignee: Rohm and Haas Company, Philadelphia, Pa.

[21] Appl. No.: 09/134,318

[22] Filed: Aug. 14, 1998

Related U.S. Application Data

[60] Provisional application No. 60/055,750, Aug. 14, 1997.

[51] Int. Cl.[7] .................................................. A01N 25/00
[52] U.S. Cl. ........................................... 424/405; 514/372
[58] Field of Search .............................. 424/405; 514/372

[56] References Cited

U.S. PATENT DOCUMENTS

| | | | |
|---|---|---|---|
| 5,468,532 | 11/1995 | Chia-Tie et al. | 428/40 |
| 5,746,814 | 5/1998 | Malhotra et al. | 106/18 |

FOREIGN PATENT DOCUMENTS

| | | |
|---|---|---|
| 0 106 563 A1 | 9/1983 | European Pat. Off. . |
| 0106 563A1 | 4/1984 | European Pat. Off. . |
| 0251 783A2 | 1/1988 | European Pat. Off. . |
| 0732052A2 | 9/1996 | European Pat. Off. . |
| 0736 249A1 | 10/1996 | European Pat. Off. . |
| 0832 561A2 | 4/1998 | European Pat. Off. . |
| WO 9625850 | 8/1996 | Germany . |
| 3020363A | 1/1991 | Japan . |
| 3054979B | 8/1991 | Japan . |
| 3258899A | 11/1991 | Japan . |
| 4082126B | 12/1992 | Japan . |

OTHER PUBLICATIONS

Morpeth, *Chemical Abstracts*, vol. 114, #201754, 1991.
Kennedy et al., *Chemical Abstracts*, vol. 85, #10385, 1976.
Kennedy et al., *Antimicrob. Agents and Chemoth.*, vol. 9, pp. 766–770, 1976.
Dubois et al., *Chemical Abstracts*, vol. 128, #8250, 1997.

*Primary Examiner*—Richard L. Raymond
*Attorney, Agent, or Firm*—Thomas D. Rogerson; S. Matthew Cairns

[57] ABSTRACT

Disclosed are solid compositions containing biocidal compounds that do not rapidly release the biocidal compounds when added to a locus to be protected and methods of controlling or inhibiting the growth of microorganisms in a locus comprising introducing into or onto the locus an effective amount of the solid compositions.

10 Claims, No Drawings

SOLID BIOCIDAL COMPOSITIONS

This application claims benefit of U.S. Provisional Application No. 60/055,750, filed Aug. 14, 1997.

BACKGROUND OF THE INVENTION

This invention relates generally to solid compositions of biocidal compounds. In particular, this invention relates to solid compositions that provide controlled release of biocidal compounds.

The ability to control release of biocidal compounds to a locus to be protected is important in the field of biocidal compounds, especially in the field of microbicides and marine antifouling agents. Typically, when a biocidal compound is added to a locus to be protected, the compound is rapidly released, whether or not it is needed. Controlled release compositions deliver the biocidal compound in a manner that more closely matches the need for the compound. In this way, only the amount of the biocidal compound needed is released into the locus to be protected. Controlled release offers the advantages of reduced cost, lowered toxicity and increased efficiency.

Solid formulations of biocidal compounds are a useful method of delivering biocidal compounds to a locus to be protected. Solid formulations also offer the advantage of safening the biocidal compound by reducing the possibility of human exposure. For example, solid compositions eliminate the splash hazard that is common with liquid compositions.

Various solid compositions of biocidal compounds are known. Such methods include encapsulation of the biocidal compound, adsorption of the biocidal compound on an inert carrier, such as silica gel, and clathration of the biocidal compound.

However, such solid compositions do not always provide controlled release of the biocidal compounds. For example, solid compositions where the biocidal compound is adsorbed on an inert solid carrier usually do not control the release of the biocidal compound. Typically, once such a solid composition is added to a locus to be protected, the biocidal compound is rapidly released. Thus, any safening of the biocidal compound provided by the solid composition is lost once the composition is added to the locus.

For example, EP 106 563 A (Melamed) discloses microbicidal compositions having a water soluble microbicide admixed with an inert, finely-divided, water-insoluble solid carrier, such as clays, inorganic silicates and silicas. These compositions do not provide controlled release of the biocidal compounds. The compounds release into the locus by dissolution, and therefore, their release is controlled by the dissolution rate of the particular biocidal compound. This application does not disclose zirconium hydroxide.

Hydroxides of certain metals, such as zirconium, titanium, iron, vanadium and tin, have been disclosed to chelate antibiotics (Kennedy et al. *Antimicrob. Agents Chemother.*, 9, 766–770 (1976)). The focus of this paper is on antibiotic immobilization. Although Kennedy et al. disclose that the metal hydroxides tested may slowly release antibiotics, Kennedy et al. do not recognize the special ability of zirconium hydroxide to control the release of biocidal compounds. The other metal hydroxides in Kennedy et al., such as titanium hydroxide, do not control the release of biocidal compounds. There is no discussion of microbicidal compounds or marine antifouling agents.

The problem addressed by the present invention is to provide solid compositions of biocidal compounds that are safer to handle and provide controlled release of biocidal compounds once the composition is added to a locus to be protected.

SUMMARY OF THE INVENTION

The present invention provides a solid composition comprising a biocidal compound and zirconium hydroxide, wherein the composition provides controlled release of the biocidal compound.

It is a further object of the invention to provide a method of controlling or inhibiting the growth of microorganisms in a locus comprising introducing into or onto the locus to be protected an effective amount of the composition described above.

It is a further object of the invention to provide a method of eliminating or inhibiting the growth of marine organisms on a structure comprising introducing into or onto the structure to be protected an effective amount of the composition described above.

DETAILED DESCRIPTION OF THE INVENTION

As used throughout the specification, the following terms shall have the following meanings, unless the context clearly indicates otherwise.

The term "biocidal compounds" refers to microbicides and marine antifouling agents. "Microbicide" refers to a compound capable of inhibiting the growth of or controlling the growth of microorganisms in a locus. The term "locus" does not include pharmaceutical or veterinary applications. The term "microorganism" includes, but is not limited to, fungi, bacteria, and algae.

"Marine antifouling agent" includes algaecides and molluscicides. "Marine antifouling activity" is intended to include the elimination of and inhibition of growth of marine organisms. Marine organisms controlled by marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones, and the term "hard fouling organisms" refers to invertebrates having some type of hard outer shell, such as barnacles, tubeworms, and molluscs.

All amounts are percent by weight ("% wt"), unless otherwise noted and all % wt ranges are inclusive. As used throughout this specification, the following abbreviations are applied: g=grams; mL=milliliter; L=liter; C=centigrade; min=minute; ppm=parts per million; rpm=revolutions per minute; and cm=centimeter.

Suitable microbicides useful in the present invention include, but are not limited to: methylenebis(thiocyanate); isothiazolones, such as 2-n-octyl-4-isothiazoin-3-one; 4,5-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; and 2-methyl-4,5-trimethylene-4-isothiazolin-3-one; carbamates, such as 3-iodopropargyl-N-butylcarbamate; methyl benzimidazol-2-ylcarbamate; imidazolidinyl urea; diazolidinyl urea; N'-[3,4-dichlorophenyl]-N,N-dimethylurea; 3,4,4'-trichlorocarbanilide; dimethyl dithiocarbamate; and disodium ethylene bisdithiocarbamate; heterocyclic compounds, such as zinc 2-pyridinethiol-1-oxide; sodium 2-pyridinethiol-1-oxide; 10,10'-oxybisphenoxyarsine; N-trichloromethylthiophthalimide; 5-oxo-3,4-dichloro-1,2-dithiol; 3-bromo-1-chloro-5,5-dimethylhydantoin; 4,4- dimethyl-1,3-dimethylolhydantoin; 2-(thiocyanomethylthio)benzothiazole; 2-methylthio-4-t-butylamino-6-cyclopropylamino-s-triazine; iodopolyvinylpyrrolidone; 3,5-dimethyl-1H-pyrazole-1-methanol; 1-(2-hydroxyethyl)-2-octadecylimidazoline; 4-(2-nitrobutyl)morpholine; triazine; N,N'-methylenebis(5-methyl-1,3-oxazolidine); 2,2'-oxybis(4,4,6-trimethyl-1,3,2-dioxaborinane); 2,2'-(1-methyltrimethylenedioxy) bis(4-ethyl-1,3,2-dioxaborinane); hexahydro-1,3,5-tris(2-hydroxyethyl)-s-triazine; 4,4-dimethyloxazolidine; 3,4,4-trimethyloxazolidine; 4,4'-(2-ethyl-nitrotrimethylene) dimorpholine; 2-methylthio-4-t-butylamino-6-cyclopropylamino-s-triazine; 2,3,5,6-tetrachloro-4-(methylsulfonyl)pyridine; alpha-[2-(4-chlorophenyl)ethyl]-alpha-(1,1-dimethylethyl)-1H-1,2,4-triazolyl-(1)-ethanol; 1-[(2-(2',4'-dichlorophenyl)-4-propyl-1,3-dioxolan-2-yl-methyl]-1H-1,2,4-triazole; didecyldimethylammonium chloride; copper-8-hydroxyquinoline; 1-[2-(2,4-dichlorophenyl)-1,3-dioxolan-2-yl-methyl]-1H-1,2,4-triazole; 2-(4-thiazolyl)-benzimidazole; 3,5-dimethyl-1,3,5-thiadiazine-2-thione; 2-chloro-4,6-bis(ethylamino)-1,3,5-triazine; 2-chloro-4-ethylamino-6-tert-butylamino-1,3,5-triazine; 1-(3-chloroallyl)-3,5,7-triaza-1-azoniaadamantane chloride; copper naphthenate; 5-hydroxymethoxymethyl-1-aza-3,7-dioxabicyclo[3.3.0]octane; 5-hydroxymethyl-1-aza-3,7-dioxabicyclo[3.3.0]octane; 7-ethyl-1,5-dioxa-3-azabicyclooctane; cetylpyridinium chloride; 3-bromo-1-chloro-5-dimethyl-5-ethylhydantoindodecyl-di(aminoethyl)-glycine; and 5-hydroxypoly-[methyleneoxyethyl]methyl-1-aza-3,7-dioxabicyclo[3.3.0] octane; carboxylic acids and their derivatives, such as (E,E)-2,4-hexadienoic acid; benzoic acid; sodium or calcium propionate; ethylenediaminetetraacetic acid disodium salt; sodium hydroxymethylglycinate; benzyl ester of 4-hydroxybenzoic acid; $(C_1-C_4)$alkyl esters of 4-hydroxybenzoic acid; $(C_1-C_4)$alkyl esters of 4-hydroxybenzoic acid sodium salts; dimethylamide of tall oil fatty acids; and 2,2-dibromo-3-nitrilopropionamide; alcohols and amines, such as 1-(alkylamino)-3-aminopropane; 2-bromo-2-nitro-1,3-propanediol; phenoxyethanol; benzyl alcohol; 2-hydroxymethylaminoethanol; n-2-hydroxypropylaminomethanol; 2-hydroxypropyl methanethiosulfonate; p-nitrophenol; and 4-chloro-3,5-dimethylphenol; ammonium and phosphonium salts, such as n-alkyl dimethyl benzylammonium chloride; cetyltrimethylammonium chloride; didecyldimethylammonium chloride; poly(hexamethylenebiguanide) hydrochloride; poly[oxyethylene(dimethyliminio) ethylene(dimethyliminio) ethylene dichloride]; alkyl dimethyl dichlorobenzylammonium chloride; dodecylguanidine hydrochloride; 2-(decylthio)ethaneamine hydrochloride; quaternary ammonium compounds; tetrakis(hydroxymethyl)phosphonium chloride; tetrakis(hydroxymethyl)phosphonium sulfate; aldehydes, ketones and formaldehyde releasers, such as pentane-1,5-dial; 1,2-benzenedicarboxaldehyde; formaldehyde; 2-bromo-4'-hydroxyacetophenone; tris (hydroxymethyl)nitromethane; and 5-bromo-5-nitro-1,3-dioxane; haolgenated aromatic compounds, such as 2,4,5,6-tetrachloroisophthalonitrile; 2,4,4'-trichloro-2'-hydroxydiphenyl ether; 2,2'-dihydroxy-5,5'-dichloro-diphenylmethane; and 1,6-di-(4'-chlorophenyldiguanide)-hexane; halogenated aliphatic compounds, such as 1,2-dibromo-2,4-dicyanobutane; diiodomethyl-p-tolysulfone; dibromonitroethane; hexachlorodimethylsulfone; alkenes, such as β-bromo-β-nitrostyrene; 1,4-bis(bromoacetoxy)-2-butene; terpene; and limonene; enzymes, such as cellulase; alpha-amylase; protease; polysaccharidase; levan hydrolase; and surfactants, such as alkyl aryl esters, polyethoxylated alcohols, polyoxyethylated ethers, phosphate esters, sulfonates, sulfonated fatty materials, sulfosuccinates, and dodecylbenzene sulfonic acids.

Suitable marine antifouling agents useful in the present invention include, but are not limited to: manganese ethylenebisdithiocarbamate; zinc dimethyl dithiocarbamate; 2-methylthio-4-t-butylamino-6-cyclopropylamino-s-triazine; 2,4,5,6-tetrachloroisophthalonitrile; 3-(3,4-dichlorophenyl)-1,1-dimethyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to, 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

Preferred biocidal compounds are 2-n-octyl-4-isothiazolin-3-one; 4,5-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; 2-methyl-4,5-trimethylene-4-isothiazolin-3-one; 3-iodopropargyl-N-butylcarbamate; zinc 2-pyridinethiol-1-oxide; sodium 2-pyridinethiol-1-oxide; 3,4,4'-trichlorocarbanilide; 2-bromo-2-nitro-1,3-propanediol; 1,2-dibromo-2,4-dicyanobutane; methylenebis(thiocyanate); 3-bromo-1-chloro-5,5-dimethylhydantoin; 2,2-dibromo-3-nitrilopropionamide; 2,4,5,6-tetrachloroisophthalonitrile; 2-(thiocyanomethylthio)benzothiazole; and 5-chloro-2-(2,4-dichlorophenoxy)phenol.

The biocidal compounds useful in this invention are generally commercially available. Zirconium hydroxide, also known as hydrous zirconia, is commercially available from Magnesium Elektron, Inc. (Flemington, N.J.). Zirconium hydroxide may be used without further purification. Zirconium hydroxide may also be used in hydrated form, such as a paste.

When the biocidal compound is a solid, the compositions of the invention may be prepared by mixing the biocidal compound, as a melt or as a solution, with the zirconium hydroxide. When the biocidal compound is a liquid, the biocidal compound may be mixed as is with the zirconium hydroxide, or mixed as a solution with the zirconium hydroxide. Suitable solvents for the biocidal compound are any which dissolve the compound, do not destabilize it and do not react with the zirconium hydroxide. Suitable solvents include alcohols, such as methanol, ethanol, and propanol; esters, such as ethyl acetate and butyl acetate; ketones, such as acetone and methyl iso-butyl ketone; nitrites, such as acetonitrile; and the like. Preferred solvents are $(C_1-C_4)$ alcohols.

The total amount of biocidal compound in the composition is 0.1% wt to 95% wt based on the weight of zirconium hydroxide. Preferably, the total amount of biocidal compound is 0.1 to 30% wt. Thus, the weight ratio of biocidal compound to zirconium hydroxide in the compositions is generally 0.1:99.9 to 95:5 and preferably 0.1:99.9 to 30:70.

For compositions of the invention comprising certain biocidal compounds, a portion of the biocidal compound may be rapidly released to a locus while the remaining portion of the biocidal compound is released in a controlled manner. When this is the case, generally up to 25 mole percent of the biocidal compound is released in a controlled manner and the excess over 25 mole percent is rapidly released. The amount that is released in a controlled manner depends upon the particular biocidal compound used. For example, when the compositions of the invention comprise generally more than 16% wt (approximately 9 mole percent) of 4,5-dichloro-2-n-octyl-3-isothiazolone, the amount of 4,5-dichloro-2-n-octyl-3-isothiazolone in excess of 16% wt is rapidly released to the locus, while the remaining 16% wt is released to the locus in a controlled manner. Generally, adding more than 25 mole percent of the biocidal compound to the compositions of the invention provides biocidal compound that is rapidly released to the locus for initial control of microorganisms and controlled release of the remaining biocidal compound for extended control of microorganisms. Compositions comprising greater than 25 mole percent of biocidal compound may be preferred for use in certain loci where both initial control and extended control are required.

More than one biocidal compound may be used in the compositions of the present invention as long as the compounds do not react with, or otherwise destabilize, each other and are compatible with the zirconium hydroxide. This has the advantage of safening multiple biocidal compounds which may provide a broader spectrum of control than one compound alone. Also, this may reduce the cost of treatment when multiple biocidal compounds must be used.

The compositions of the invention are useful wherever the biocidal compound would be useful. When the biocidal compound is a microbicide, the compositions of the invention are useful in controlling or inhibiting the growth of microorganisms, such as bacteria, fungi and algae, in a locus. The compositions of the invention are suitable for use in any locus requiring protection from microorganisms. Suitable loci include, but are not limited to: cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood, including lumber, timber, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids; coatings, including marine coatings; petroleum processing fluids; fuel; oil field fluids; photographic chemicals; printing fluids; sanitizers; detergents; textiles; and textile products.

When compositions of the invention comprise a microbicide, they can either be added directly to the locus to be protected or added as a composition further comprising a suitable carrier. Suitable carriers useful for microbicidal applications include, but are not limited to, water; organic solvent, such as ethylene glycol, diethylene glycol, propylene glycol, dipropylene glycol, xylene, toluene, acetone, methyl isobutyl ketone, or esters; or mixtures thereof. The compositions may also be formulated as microemulsions, microemulsifiable concentrates, emulsions, emulsifiable concentrates, pastes, or may be encapsulated. The particular formulation will depend upon the locus to be protected and the particular microbicide used. The preparation of these formulations are by well known, standard methods.

When the compositions comprise a microbicide, the amount of the compositions of the invention necessary to control or inhibit the growth of microorganisms depends upon the locus to be protected, but is typically sufficient if it provides 0.1 to 5000 ppm of microbicide, at the locus to be protected. Microbicides are often used in loci that require further dilution. For example, the compositions of the invention may be added to a metal working fluid concentrate, which is then further diluted. The amount of the compositions of the invention necessary to control microorganism growth in the final metal working fluid dilution are sufficient if they provide generally 5 to 50 ppm of the microbicide in the final dilution. In loci such as a paint, which is not further diluted, the amount of the compositions of the invention necessary to control microorganism growth are sufficient if they provide generally 500 to 5000 ppm of the microbicide.

When the biocidal compound of the present invention is a marine antifouling agent, the compositions of the present invention can be used to inhibit the growth of marine organisms by application of the compositions onto or into a marine structure. Depending upon the particular marine structure to be protected, the compositions of the present invention can be directly incorporated into the marine structure, applied directly to the marine structure, or incorporated into a coating which is then applied to the marine structure.

Suitable structures include, but are not limited to: boats, ships, oil platforms, piers, pilings, docks, elastomeric rubbers, and fish nets. The compositions of the present invention are typically directly incorporated into structures such as elastomeric rubber or fish net fibers during manufacture. Direct application of the compositions of the invention is typically made to structures such as fish nets or wood pilings. The compositions of the invention can also be incorporated into a marine coating, such as a marine paint or varnish.

When the compositions of the present invention comprise a marine antifouling agent, the amount of the compositions of the invention necessary to inhibit or prevent the growth of marine organisms is typically sufficient if it provides 0.1 to 30% wt of marine antifouling agent, based on the weight of the structure to be protected or based on the weight of the coating to be applied. When the compositions of the invention are directly incorporated into or directly applied onto a structure, the amount of the compositions necessary to inhibit the growth of marine organisms is generally sufficient if it provides 0.1 to 30% wt of marine antifouling agent, based on the weight of the structure. It is preferred that the amount of the compositions of the invention be sufficient to provide 0.5 to 20% wt of marine antifouling agent; more preferably, 1 to 15% wt. When incorporated into a coating, the amount of the compositions of the invention suitable to inhibit the growth of marine organisms is generally sufficient if it provides 0.1 to 30% wt of marine antifouling agent, based on the weight of said coating. The amount of the compositions of the invention preferably provides 0.5 to 15% wt of marine antifouling agent; more preferably, 1 to 10% wt.

In general, the compositions of the invention comprising a marine antifouling agent are incorporated in a carrier such as water; organic solvent, such as xylene, methyl isobutyl ketone, and methyl isoamyl ketone; or mixtures thereof.

Direct applications of the compositions of the present invention may be by any conventional means, such as dipping, spraying, or coating. Fish nets, for example, may be also protected by dipping the fish nets into a composition comprising the compositions of the invention and a carrier or by spraying the fish nets with the composition.

Structures such as wood pilings and fish nets may be protected by directly incorporating the compositions of the invention into the structure. For example, a composition of the invention further comprising a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The compositions of the invention are suitable for use in both solvent and water based marine coatings. Solvent based marine coatings are preferred.

Any conventional binder may be utilized in the marine antifouling coating incorporating the compositions of the invention. Suitable binders include, but are not limited to: polyvinyl chloride in a solvent based system; chlorinated rubber in a solvent based system; acrylic resins in solvent based or aqueous systems; vinyl chloride-vinyl acetate copolymer systems as aqueous dispersions or solvent based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and natural resins, such as rosin. Water based coatings may also optionally contain: coalescents, dispersants, surface active agents, rheology modifiers, or adhesion promoters. Solvent based coatings may also optionally contain extenders, plasticizers, or rheology modifiers.

A typical marine coating comprises 2 to 20% wt binders, up to 15% wt rosins/modified rosins, 0.5 to 5% wt plasticizers, 0.1 to 2% wt antisettling agent, 5 to 60% wt solvent/diluent, up to 70% wt cuprous oxide, up to 30% wt pigments (other than cuprous oxide), and up to 15% wt marine antifouling agent.

Marine coatings containing the compositions of the invention may be applied to a structure to be protected by any of a number of conventional means. Suitable means of application include, but are not limited to, spraying; rolling; brushing; or dipping.

The following examples are presented to illustrate further various aspects of the present invention, but are not intended to limit the scope of the invention in any aspect.

EXAMPLE 1

Preparation of Compositions of the Invention

The compositions of the invention were prepared by the following general method.

To 1.0 g of zirconium hydroxide in a flask were added 0.7 g of a 20% wt solution of 4,5-dichloro-2-n-octyl-3-isothiazolone in methanol. The resulting slurry was then dried under reduced pressure at 55° C. to yield 1.1 g of a yellow powder. The composition, labeled as Sample 1, contained 14% wt of 4,5-dichloro-2-n-octyl-3-isothiazolone based on the total weight of zirconium hydroxide. These data are reported in Table 1.

Table 1 shows other compositions prepared according to the above general method, except that the isothiazolone was changed or the amount of isothiazolone solution added was changed.

TABLE 1

Compositions of the Invention

| Sample | Isothiazolone | % Wt |
|---|---|---|
| 1 | 4,5-dichloro-2-n-octyl-3-isothiazolone | 14 |
| 2 | 4,5-dichloro-2-n-octyl-3-isothiazolone | 16 |
| 3 | 4,5-dichloro-2-n-octyl-3-isothiazoone | 28 |
| 4 | 2-n-octyl-3-isothiazolone | 14 |
| 5 | 2-n-octyl-3-isothiazolone | 28 |
| 6 | 3:1 mixture of 5-chloro-2-methyl-3-isothiazolone and 2-methyl-3-isothiazolone | 15 |
| 7 | 3,4,4'-trichlorocarbanilide | 33 |

EXAMPLE 2

Release of Biologically Active Compound

Sample 1 and a comparative sample were evaluated for their release of biocidal compound.

Comparative sample 1 ("C-1") was prepared according to the general method of Example 1, except that silica gel was substituted for zirconium hydroxide. Samaple C-1 contained 14% wt of 4,5-dichloro-2-n-octyl-3-isothiazolone.

The amount of biocidal compound released from each sample was determined according to the following general procedure. A weighed amount of sample was placed in a 100 mL sample jar. To the jar was then added 100 mL of water containing 0.3% wt of sodium diethylhexylsulfosuccinate. The solution was then gently stirred to ensure no foam was formed. Aliquots (0.5 mL) were taken at various time points and transferred to a microcentrifuge tube. Each aliquot was then centrifuged at 14,000 rpm for 3 minutes. The supernatent was then removed and analyzed by HPLC for the amount of the biocidal compound. The microcentrifuge tube was then washed with 0.5 mL of water containing 0.3% of sodium diethylhexylsulfosuccinate and the wash liquid added to the sample jar. This ensured that none of the particles removed during sampling were lost and that the volume in the jar remained constant. The cumulative percentage of 4,5-dichloro-2-n-octyl-3-isothiazolone released is reported in Table 2.

TABLE 2

| Percentage of 4,5-Dichloro-2-n-octyl-3-isothiazolone Released | | | | | |
|---|---|---|---|---|---|
| Sample | 20 Min. | 40 Min. | 60 Min. | 120 Min. | 180 Min. |
| 1 | 1.5 | 1.5 | 1.5 | 1.5 | 2.5 |
| C-1 | 50.5 | 53.5 | 75 | 77 | 72 |

The above data clearly show that the compositions of the present invention greatly control the release of 4,5-dichloro-2-n-octyl-3-isothiazolone as compared to other known solid compositions.

EXAMPLE 3

Comparative

A comparative solid composition of a biocidal compound with titanium (IV) hydroxide was prepared and evaluated.

To 1.06 g of titanium (IV) hydroxide were added 1.03 g of a 20.4% wt solution of 4,5-dichloro-2-n-octyl-3- isothiazolone in ethanol. The resulting slurry was homogenized in 10 mL of ethanol. The solvent was then removed under reduced pressure at room temperature for 1 hour and then at 45° C. for 1 hour. The resulting powder, labeled C-2, contained 20% wt of 4,5-dichloro-2-n-octyl-3-isothiazolone. Sample C-2 was evaluated for its ability to release the 3-isothiazolone according to the procedure of Example 2. The cumulative percentages of 4,5-dichloro-2-n-octyl-3-isothiazolone released are reported in Table 3.

TABLE 3

Percentage of 4,5-Dichloro-2-n-octyl-3-isothiazolone Released

| Sample | 30 Min. | 60 Min. | 120 Min. | 300 Min. | 1860 Min. | 5760 Min. |
|---|---|---|---|---|---|---|
| C-2 | 4.9 | 7.2 | 11.0 | 19.7 | 50.3 | 68.4 |

The above data clearly show that the titanium (IV) hydroxide solid composition rapidly releases 4,5-dichloro-2-n-octyl-3-isothiazolone as compared to the compositions of the present invention, and does not provide any controlled release of 4,5-dichloro-2-n-octyl-3-isothiazolone.

EXAMPLE 4

Comparative

A comparative solid composition of a biocidal compound with zirconium oxide was prepared and evaluated.

Zirconium oxide was prepared by calcining zirconium hydroxide at 500° C. To 2.0 g of zirconium oxide were added 2.86 g of a 10% wt solution of 4,5-dichloro-2-n-octyl-3-isothiazolone in methanol. The solvent was then removed under reduced pressure to yield a light yellow powder. The resulting powder, labeled sample C-3, contained 14% wt of 4,5-dichloro-2-n-octyl-3-isothiazolone. Sample C-3 was evaluated for its ability to release the 3-isothiazolone according to the procedure of Example 2. The cumulative percentages of 4,5-dichloro-2-n-octyl-3-isothiazolone released are reported in Table 4.

TABLE 4

Percentage of 4,5-Dichloro-2-n-octyl-3-isothiazolone Released

| Sample | 20 Min. | 40 Min. | 60 Min. | 130 Min. | 180 Min. | 300 Min. |
|---|---|---|---|---|---|---|
| C-3 | 85 | 79 | 91 | 92 | 94 | 95 |

The above data clearly show that the zirconium oxide solid composition rapidly releases 4,5-dichloro-2-n-octyl-3-isothiazolone as compared to the compositions of the present invention, and does not provide any controlled release of 4,5-dichloro-2-n-octyl-3-isothiazolone.

EXAMPLE 5

Mildewcidal Activity

The compositions of the invention were evaluated for mildewcidal activity in a paint formulation.

The paint formulation was prepared by milling the following ingredients for 10 to 15 minutes in a Cowles Dissolver at 3800–4500 rpm.

| Material | g/L |
|---|---|
| Natrosol 250 MHR hydroxyethyl cellulose | 3.6 |
| Ethylene glycol | 30 |
| Water | 134.4 |
| Tamol 960 (40%) poly(methacrylic acid) | 8.6 |
| Triton CF-10 surfactant | 3.1 |
| Colloid 643 defoamer | 1.2 |
| Propylene glycol | 40.8 |
| Ti-Pure R-902 titanium dioxide | 270 |
| Minex 4 filler pigment | 191.3 |
| Icecap K filler pigment | 60 |
| Attagel 50 clay | 6 |

Once the above components were milled, the following components were added at a slower speed.

| Material | g/L |
|---|---|
| Film forming acrylic copolymer | 367.1 |
| Colloid 643 defoamer | 3.6 |
| Texanol coalescent | 11.3 |
| Ammonia (28%) | 2.8 |
| Natrosol 250 MHR hydroxyethyl cellulose | 128.4 |
| Water | 130.8 |

Sufficient mildewcide was added to the paint formulation to give either 1000, 5000, 6000, or 30,000 ppm biocidal compound.

Paint samples were prepared using the compositions of the invention of Samples 1, 2 and 4. These paints were tested for mildew resistance and compared with paints containing zirconium hydroxide alone ("Sample C-4"), 4,5-dichloro-2-n-octyl-3-isothiazolone alone ("Sample C-5"), and 2-n-octyl-3-isothiazolone alone ("Sample C-6"). The actual amounts of the biocidal compounds used are reported in Tables 5 and 6.

The paints were tested according to the following general procedure. Analytical 1.27 cm (0.5 inch) filter paper discs were dipped into the paint sample to be tested, the excess paint wiped off, and the circle placed on a Beckman modular reservoir. The painted discs were then dried at room temperature for 24 hours.

Some of the dried discs were subjected to a leaching test to simulate a wet environment. The dried discs on the reservoirs were placed in a water bath with running water. After various times, the discs were removed from the water bath and dried at room temperature.

After all the discs had been removed and dried, the discs were placed on a malt agar plate (25.4×25.4 cm) and then inoculated with a mixture of five fungi: *Aspergillus niger, Aureobasidium pullulans, Cladosporium cadosporiodes, Penicillium purpurogenum,* and *Stachybotrys chartrum.* The inoculated plates were then incubated at 30° C. for one week. After one week, the discs were visually rated for fungal growth on a scale of 1–10, where 10 is no growth and 1 is complete fungal overgrowth. Ratings of 9 and 10 are passing. The results are reported in Table 5.

The remaining discs were subjected to conditions of high heat. The remaining discs on the reservoirs were placed in a 50° C. oven. After various times, the discs were removed from the oven. After all the discs had been removed from the oven, the discs were inoculated with the fungal mixture as described above. The results are reported in Table 6.

TABLE 5

Fungal Resistance After Days Leaching

| Samle | ppm | Day 0 | Day 6 | Day 8 | Day 11 | Day 13 |
|---|---|---|---|---|---|---|
| 1 | 1000 | 10 | 3 | 3 | 1 | 1 |
| 1 | 5000 | 10 | 10 | 9 | 9 | 9 |
| Control* | — | 6 | 1 | 1 | 1 | 1 |
| C-4 | 6000 | 2 | — | — | — | — |
| C-4 | 30,000 | 2 | — | — | — | — |

*The control was a paint that contained no biocidal compound.

TABLE 6

Fungal resistance After Days Heating

| Samle | ppm | Day 0 | Day 4 | Day 10 | Day 25 |
|---|---|---|---|---|---|
| 2 | 1000 | 10 | 10 | 6 | 4 |
| 3 | 1000 | 10 | 10 | 8 | 6 |
| 4 | 1000 | 10 | 10 | 10 | 10 |
| C-5 | 1000 | 10 | 10 | 10 | 5 |
| C-6 | 1000 | 10 | 10 | 10 | 10 |

These data clearly show that 4,5-dichloro-2-n-octyl-3-isothiazolone and 2-isothiazolone retain their mildewcidal activity when prepared as solid compositions according to the present invention. These data also show that zirconium hydroxide does not provide any mildewcidal activity.

What is claimed:

1. A solid composition comprising zirconium hydroxide and a biocidal compound selected from the group consisting of 2-n-octyl-4-isothiazolin-3-one; 4,5-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; 2-methyl-4,5-trimethylene-4-isothiazolin-3-one; zinc 2-pyridinethiol-1-oxide; sodium 2-pyridinethiol-1-oxide; 3,4,4'-trichlorocarbanilide; 2-bromo-2-nitro-1,3-propanediol; 1,2-dibromo-2,4-dicyanobutane; methylenebis(thiocyanate); 3-bromo-1-chloro-5,5-dimethylhydantoin; 2,2-dibromo-3-nitrilopropionamide; 2,4,5,6-tetrachloroisophthalonitrile; 2-(thiocyanomethylthio)benzothiazole; 5-bromo-5-nitro-1,3-dioxane; 4,4-dimethyl-1,3-dimethylolhydantoin; didecyldimethylammonium chloride; cetylpyridinium chloride; n-alkyl dimethyl benzylammonium chloride; cetyltrimethylammonium chloride; didecyldimethylammonium chloride; poly(hexamethylenebiguanide) hydrochloride; poly(oxyethylene(dimethyliminio) ethylene(dimethyliminio)ethylene dichloride); alkyl dimethyl dichlorobenzylammonium chloride; dodecylguanidine hydrochloride; 2-(decylthio)ethaneamine hydrochloride; tetrakis(hydroxymethyl)phosphonium chloride; tetrakis(hydroxymethyl)phosphonium sulfate and mixtures thereof, wherein the composition provides controlled release of the biocidal compound.

2. The composition of claim 1 wherein the biocidal compound is selected from the group consisting of 2-n-octyl-4-isothiazolin-3-one; 4,5-dichloro-2-n-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; 2-methyl-4,5-trimethylene-4-isothiazolin-3-one; zinc 2-pyridinethiol-1-oxide; sodium 2-pyridinethiol-1-oxide; 3,4,4'-trichlorocarbanilide; 2-bromo-2-nitro-1,3-propanediol; 1,2-dibromo-2,4-dicyanobutane; methylenebis(thiocyanate); 3-bromo-1-chloro-5,5-dimethylhydantoin; 2,2-dibromo-3-nitrilopropionamide; 2,4,5,6-tetrachloroisophthalonitrile; 2-(thiocyanomethylthio)benzothiazole; 5-chloro-2-(2,4-dichlorophenoxy)phenol; 5-bromo-5-nitro-1,3-dioxane; and mixtures thereof.

3. The composition of claim 1 wherein the weight ratio of biocidal compound to zirconium hydroxide is from 0.1:99.9 to 95:5.

4. The composition of claim 3 wherein the weight ratio is from 0.1:99.9 to 30:70.

5. The composition of claim 1 further comprising a carrier selected from the group consisting of water, acetonitrile, ethyl acetate, butyl acetate, toluene, xylene, methanol, ethanol, acetone, methyl ethyl ketone, methyl isobutyl ketone, ethylene glycol, diethylene glycol, propylene glycol, and dipropylene glycol.

6. The composition of claim 1 wherein the biocidal compound is selected from the group consisting of 4,5-dichloro-2-n-octyl-3-isothaizolone; 2-n-octyl-3-isothaizolone; 3:1 mixture of 5-chloro-2-methyl-3-isothiazolone and 2-methyl-3-isothiazolone; and 3,4,4'-trichlorocarbanilide.

7. A method of controlling the release of a biocidal compound selected from the group consisting of 2-n-octyl-4-isothiazolin-3-one; 4,5-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; 2-methyl-4,5-trimethylene-4-isothiazolin-3-one; 3-iodopropargyl-N-butylcarbamate; zinc 2-pyridinethiol-1-oxide; sodium 2-pyridinethiol-1-oxide; 3,4,4'-trichlorocarbanilide; 2-bromo-2-nitro-1,3-propanediol; 1,2-dibromo-2,4-dicyanobutane; methylenebis(thiocyanate); 3-bromo-1-chloro-5,5-dimethylhydantoin; 2,2-dibromo-3-nitrilopropionamide; 2,4,5,6-tetrachloroisophthalonitrile; 2-(thiocyanomethylthio)benzothiazole; 5-bromo-5-nitro-1,3-dioxane; 4,4-dimethyl-1,3-dimethylolhydantoin; didecyldimethylammonium chloride; cetylpyridinium chloride; n-alkyl dimethyl benzylammonium chloride; cetyltrimethylammonium chloride; didecyldimethylammonium chloride; poly(hexamethylenebiguanide) hydrochloride; poly(oxyethylene(dimethyliminio) ethylene(dimethyliminio) ethylene dichloride); alkyl dimethyl dichlorobenzylammonium chloride; dodecylguanidine hydrochloride; 2-(decylthio)ethaneamine hydrochloride; tetrakis(hydroxymethyl)phosphonium chloride; tetrakis(hydroxymethyl)phosphonium sulfate and mixtures thereof, comprising the step of mixing the biocidal compound with zirconium hydroxide.

8. A method for controlling the growth of bacteria, fungi, algae and marine fouling organisms comprising introducing to a locus to be protected the composition of claim 1.

9. The method of claim 8 wherein the locus to be protected is selected from cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood, including lumber, timer, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids; coatings, including marine coatings; petroleum processing fluids; fuel; oil field fluids; photographic chemicals; printing fluids; sanitizers; detergents; textiles, textile products; and marine structures.

10. The method of claim 9 wherein the marine structure is selected from the group consisting of boats, ships, oil platforms, piers, pilings, docks, elastomeric rubbers, and fish nets.

* * * * *